United States Patent
Angeletakis et al.

(10) Patent No.: US 6,890,968 B2
(45) Date of Patent: *May 10, 2005

(54) PREPOLYMERIZED FILLER IN DENTAL RESTORATIVE COMPOSITE

(75) Inventors: Christos Angeletakis, Orange, CA (US); Minh-Dang Son Nguyen, Orange, CA (US); Alvin I. Kobashigawa, Fountain Valley, CA (US)

(73) Assignee: Kerr Corporation, Orange, CA (US)

( * ) Notice: Subject to any disclaimer, the term of this patent is extended or adjusted under 35 U.S.C. 154(b) by 388 days.

This patent is subject to a terminal disclaimer.

(21) Appl. No.: 10/234,594

(22) Filed: Sep. 4, 2002

(65) Prior Publication Data

US 2003/0032693 A1 Feb. 13, 2003

Related U.S. Application Data

(63) Continuation-in-part of application No. 09/859,106, filed on May 16, 2001, now Pat. No. 6,593,395.

(51) Int. Cl.$^7$ .......................... A61K 6/083; C08K 3/22; C08K 3/34; A61C 13/08
(52) U.S. Cl. ...................... 523/115; 523/113; 523/116; 523/118; 523/217; 106/35; 433/228.1
(58) Field of Search ................................. 523/115, 113, 523/116, 118, 217; 106/35; 433/228.1

(56) References Cited

U.S. PATENT DOCUMENTS

| | | | |
|---|---|---|---|
| 4,389,497 A | 6/1983 | Schmitt et al. | 523/116 |
| 4,503,169 A | 3/1985 | Randkiev | 523/117 |
| 4,781,940 A | 11/1988 | Denton, Jr. | 427/2 |
| 5,192,815 A | 3/1993 | Okada et al. | 523/115 |
| 5,460,701 A | 10/1995 | Parker et al. | 204/164 |
| 5,514,349 A | 5/1996 | Parker et al. | 422/186.21 |
| 5,609,675 A | 3/1997 | Noritake et al. | 106/35 |
| 5,610,712 A | 3/1997 | Schmitz et al. | 356/335 |
| 5,788,738 A | 8/1998 | Pirzada et al. | 75/331 |
| 5,851,507 A | 12/1998 | Pirzada et al. | 423/659 |
| 5,874,684 A | 2/1999 | Parker et al. | 75/228 |
| 5,936,006 A | 8/1999 | Rheinberger et al. | 523/116 |
| 5,979,805 A | 11/1999 | Angeletakis | 241/21 |
| 5,984,997 A | 11/1999 | Bickmore et al. | 75/343 |
| 6,010,085 A | 1/2000 | Angeletakis | 241/21 |
| 6,020,395 A | 2/2000 | Angeletakis | 523/116 |
| 6,098,906 A | 8/2000 | Angeletakis | 241/21 |
| 6,121,344 A | 9/2000 | Angeletakis et al. | 523/116 |
| 6,127,450 A | 10/2000 | Angeletakis | 523/116 |
| 6,194,481 B1 | 2/2001 | Furman et al. | 522/77 |
| 6,196,843 B1 | 3/2001 | Kawaguchi et al. | 433/212.1 |
| 6,232,367 B1 | 5/2001 | Kobashigawa et al. | 523/116 |
| 6,300,390 B1 | 10/2001 | Angeletakis | 523/116 |
| 6,306,927 B1 | 10/2001 | Blackwell et al. | 523/116 |
| 6,359,090 B1 | 3/2002 | Angeletakis | 526/277 |
| 6,572,693 B1 * | 6/2003 | Wu et al. | 106/35 |
| 6,593,395 B2 * | 7/2003 | Angeletakis et al. | 523/115 |

FOREIGN PATENT DOCUMENTS

| | | |
|---|---|---|
| EP | 0368657 | 5/1990 |
| EP | 1 050 291 A2 | 11/2000 |
| EP | 1 234 567 A2 | 8/2002 |
| WO | WO 99/65453 | 12/1999 |
| WO | WO 00/61073 | 10/2000 |
| WO | WO 01/26611 | 4/2001 |
| WO | WO 01/30304 | 5/2001 |
| WO | WO 01/30305 | 5/2001 |
| WO | WO 01/30306 | 5/2001 |
| WO | WO 01/30307 | 5/2001 |

* cited by examiner

Primary Examiner—Tae H. Yoon
(74) Attorney, Agent, or Firm—Wood, Herron & Evans, LLP (57) ABSTRACT

A dental composite having high filler loading and low shrinkage thereby providing good strength and marginal integrity. Through the use of prepolymerized filler particles in combination with a structural filler and a nanofiller, the composite exhibits very low shrinkage and is useful in stress bearing restorations and in cosmetic restorations. The structural filler used is ground to a mean particle size of less than 0.5 μm and the nanofiller has discrete particles of a mean particle size less than 100 nm to improve handling and mechanical characteristics. The prepolymerized filler particles also allow for less viscosity and better handling characteristics of the composite.

49 Claims, 1 Drawing Sheet

PREPOLYMERIZED FILLER IN DENTAL RESTORATIVE COMPOSITE

RELATED APPLICATIONS

The present application is a continuation-in-part of application Ser. No. 09/859,106, filed May 16, 2001, now U.S. Pat. No. 6,593,395 which is incorporated by reference herein in its entirety.

FIELD OF THE INVENTION

The present invention generally relates to composite resin materials for use in dental restorations, and more particularly to a universal composite resin material incorporating a structural filler, a prepolymerized filler, and a discrete nano-particle sized filler to provide a composite of high strength, improved loading and reduced shrinkage in clinical use.

BACKGROUND OF THE INVENTION

In dentistry, practitioners use a variety of restorative materials, for example to create crowns, veneers, direct fillings, inlays, onlays and splints. Composite resins are a type of restorative material which are suspensions of strengthening agents, such as mineral filler particles, in a resin matrix. These materials may be dispersion reinforced, particulate reinforced, or hybrid composites.

Dispersion reinforced composites include a reinforcing filler having a mean particle size of about 0.05 μm or less, with a filler loading of about 30%–45% by volume. However, loading of the dispersion-reinforcing filler into the resin is limited by the ability of the resin to wet the filler due to the small particle size and high surface area of this type of reinforcing filler. Consequently, the filler loading is limited to about 45% by volume. Due to the low loading, the filler particles are not substantially in contact with one another. Thus, the primary reinforcing mechanism of such dispersion-reinforced composites is by dislocation of flaws in the matrix around the filler. In dispersion-reinforced materials, the strength of the resin matrix contributes significantly to the total strength of the composite. In dentistry, dispersion reinforced composite resins or microfills are typically used for cosmetic restorations due to their ability to retain surface luster. Typically, these microfill resins use free radical-polymerizable resins such as methacrylate monomers, which, after polymerization, are much weaker than the dispersed filler. Despite the dispersion reinforcement, microfill resins are structurally weak, limiting their use to low stress restorations.

Microfills generally use prepolymerized filler material for dispersion reinforcement, as described in U.S. Pat. Nos. 4,389,497, 4,781,940 and 6,020,395. Generally, prepolymerized filler is produced by mixing finely divided silica with a polymerizable monomer, heat polymerizing the mixture in bulk, and pulverizing or grounding the mixture down to the desired agglomerate size to give a filler material comprising splintered polymerized particles. Polymerized particle sizes are large, generally greater than 1 μm in diameter, allowing for better reinforcement but a less stable, less glossy surface. The polymerized particles or prepolymerized filler material is then mixed with a polymerizable monomer, typically an acrylate or methacrylate-based resin, and an additional filler material, such as colloidal or fumed silica, to form the final microfill dental composite.

Particulate reinforced composites typically include a reinforcing filler having an average particle size greater than about 0.6 μm and a filler loading of about 60% by volume. At these high filler loadings, the filler particles begin to contact one another and contribute substantially to the reinforcing mechanism due to the interaction of the particles with one another and to interruption of flaws by the particles themselves. These particulate reinforced composite resins are stronger than microfill resins. As with the dispersion-reinforced composites, the resin matrix typically includes methacrylate monomers. However, the filler in particulate reinforced composites has a greater impact on the total strength of the composite, such that the particulate reinforced composites have been used for stress bearing restorations.

Another class of dental composites, known as hybrid composites, include the features and advantages of dispersion reinforcement and those of particulate reinforcement. Hybrid composite resins contain fillers having an average particle size of 0.6 μm or greater with a microfiller having an average particle size of about 0.05 μm or less. HERCULITE® XRV (Kerr Corp.) is one such example. HERCULITE® has been considered by many as an industry standard for hybrid composites. It has an average particle size of 0.84 μm and a filler loading of 57.5% by volume. The filler is produced by a wet milling process that produces fine particles that are substantially contaminant free. About 10% of this filler exceeds 1.50 μm in average particle size. In clinical use, the surface of HERCULITE® turns to a semi-glossy matte finish over time. Because of this, the restoration may become distinguishable from normal tooth structure when dry, which is not desirable for a cosmetic restoration.

Various methods of forming submicron particles, such as precipitation or sol gel methods, are available to produce particulate reinforcing fillers for hybrid composites. However, these methods do not restrict the particle size to at or below the wavelength of light (about 0.5 μm) to produce a stable glossy surface. U.S. Pat. No. 6,121,344, which is incorporated by reference herein in its entirety, describes a resin-containing dental composite including a structural filler of ground particles having an average particle size of between about 0.05 μm and about 0.5 μm that has the high strength required for load-bearing restorations. Because the structural filler particles are ground, the particles are nonspherical, providing increased adhesion of the resin to the structural filler, thereby further enhancing the overall strength of the composite. Through the use of ground structural filler particles having an average particle size less than the wavelength of light, the dental composite exhibits the luster and translucency required for cosmetic restorations.

In U.S. Pat. No. 6,121,344, fumed silica having an average particle size less than about 0.05 μm are added, preferably between about 1% by weight and about 15% by weight of the composite. The microfill particles contribute to dispersion reinforcement, fill the interstices between the larger structural filler particles reducing occluded volume, and provide a large surface area to be wetted by the resin to increase strength. The fumed silica microfill particles also contribute to the flow properties of the uncured resin. Fumed silica is produced by hydrolysis of silicon tetrachloride vapor in a flame of hydrogen and oxygen. During this process, silicon dioxide molecules condense to form particles of size usually less than 50 nm. The particles then attach to each other and sinter together. Due to the nature of the flame process, a three-dimensional chain aggregate with a length of 200–300 nm forms. Further mechanical entanglement occurs upon cooling to give agglomerates. Attractive interactions between surface silanol groups of the particles give thixotropic properties to liquids in which these fumed silicas are suspended. The fumed silicas are hydrophobically treated to make it compatible with resins employed, however, treatment is usually not complete and residual unreacted silanol groups typically remain, resulting in substantial interactions of these groups with other reactive groups in the composite. The particle-particle interaction prevents homogenous dispersion of the microfiller in the resin matrix and increases the viscosity of the suspension, which correspondingly decreases the workability of the composite paste. This places a limitation on the practical filler loading in fumed silica microfilled restorative composites. A high filler loading is desirable in dental restorations because the high loading provides a paste with improved handling properties over a paste with low filler loading. Moreover, higher loading gives a composite that experiences lower shrinkage upon curing and has a coefficient of thermal expansion better matching that of a natural tooth.

Resin shrinkage upon polymerization, however, is a problem that has faced composites of the prior art incorporating dispersion reinforced, particulate reinforced and hybrid filler materials. The resin matrix shrinks upon polymerization during the curing process. Polymerization shrinkage, both axial and volumetric, generally results from the conversion of the carbon-carbon double bonds of low molecular weight monomers in the polymeric composite to corresponding carbon-carbon single bonds of crosslinked polymers during the curing reaction. Such shrinkage tends to cause gap formation between the restorative composite and the tooth, leading to microleakage, secondary caries and decreased longevity of the repair.

There is thus a need to develop a hybrid dental restorative composite that has a physical make-up to afford high filler loading, appropriate viscosity for good workability of the composite paste, and lower shrinkage during polymerization.

SUMMARY OF THE INVENTION

The present invention provides resin-containing dental composites that have high filler loading and reduced shrinkage while being mechanically strong and effective for stress bearing and cosmetic restorations without exhibiting the drawbacks of the prior art dental composites. To this end, a resin-containing dental composite is provided which includes a structural filler of ground particles having an average particle size of between about 0.05 $\mu$m and about 0.5 $\mu$m, a prepolymerized filler, and a nanofiller having discrete, non-agglomerated particles of mean particle size less than about 100 nm. Also provided is a method for making a dental composite paste and a method for restoring a tooth using said paste.

The structural filler comprises between about 10% and about 70% by volume of the composite, and advantageously between about 20% and about 60% by volume, and because the structural filler is ground, the particles are non-spherical, providing increased adhesion of the resin to the structural filler thereby enhancing the overall strength of the composite. Further, by virtue of the particles having a mean particle size less than the wavelength of light, that is less than about 0.5 $\mu$m, the structural filler contributes to the luster and translucency of the composite required for cosmetic restorations. In an exemplary embodiment, the ground structure filler contains less than 50% by volume of particles above 0.5 $\mu$m in diameter.

The discrete, non-agglomerated nanofiller particles comprise at least about 0.01% by volume of the composite, and advantageously between about 1% and about 15% by volume, and contribute to dispersion reinforcement, fill the interstices between the larger structural filler particles reducing occluded volume, and provide a large surface area to be wetted by the resin to increase strength. In addition, particle-particle interactions are minimized, thereby allowing for high filler loading and lower shrinkage upon curing.

The prepolymerized filler comprises at least about 1% by volume of the composite, and advantageously about 1% to about 60% by volume, and allows for an increased total filler loading in the composite by virtue of the low surface area of the prepolymerized filler relative to the other fillers. The prepolymerized filler particles are prepared by mixing an inorganic filler with an organic polymerizable resin and curing the mixture. The cured mixture is then ground to a desired size, for example a bimodal particle size distribution including a fine particle fraction of mean particle size in the range of about 1 $\mu$m to about 3 $\mu$m and a coarse particle fraction of mean particle size in the range of about 30 $\mu$m to about 70 $\mu$m, at least about 95% of the particles of size less than about 100 $\mu$m. The ground bimodal prepolymerized filler may be further air classified to separate the fine particle fraction from the coarse particle fraction to provide the prepolymerized filler with a coarse particle size distribution including a mean particle size in the range of about 30 $\mu$m to about 70 $\mu$m, at least about 90% of the particles of size less than about 100 $\mu$m, and at least about 85% of the particles of a size greater than about 10 $\mu$m. The prepolymerized filler enhances the polydispersity of the composite paste, thereby enabling the higher filler loading and improving the handling properties of the paste. The non-spherical surface of the ground particles provides additional adhesion between the prepolymerized filler and the resin, thereby further strengthening the cured composite. Further, a reduction in shrinkage upon curing of the composite is provided by virtue of inclusion of the prepolymerized filler, thereby increasing the tooth-composite marginal integrity.

BRIEF DESCRIPTION OF THE DRAWINGS

The present invention will now be described, by way of example, with reference to the accompanying drawings, in which.

DETAILED DESCRIPTION OF THE INVENTION

The present invention provides a dental restorative composite comprising a ground structural filler having a mean particle size between about 0.05 $\mu$m and about 0.50 $\mu$m, a prepolymerized filler, and a discrete nanofiller having a mean particle size less than about 100 nm in a curable resin, such as a resin containing polymerizable methacrylate monomers. Generally, the resinous composite is cured by mixing two paste components containing a catalyst and an accelerator, respectively, or by a photopolymerization process wherein the resins are exposed to actinic radiation, such as blue visible light. Photopolymerizable resins containing monomers other than methacrylates, such as cationically photocurable oxiranes, for example, may be used in the present invention as persons of ordinary skill in the art would appreciate. The resinous dental composite is generally applied to one or more teeth by the dental practitioner and cured by exposure to visible light. The composite cures with a low shrinkage, such as about 2% or less, which is a significant improvement over prior hybrid composites.

To provide the ground structural filler having a mean particle size of less than 0.5 $\mu$m, an extensive comminution step is required. Comminution may be performed in an agitator mill, and advantageously an agitator mill designed to minimize contamination, such as that described in U.S. Pat. No. 6,010,085, incorporated herein by reference in its entirety. Alternatively, comminution may be performed in a vibratory mill, and advantageously in a vibratory mill designed to minimize contamination, such as described in U.S. Pat. Nos. 5,979,805 and 6,098,906, each incorporated herein by reference in its entirety. Comminution deagglomerates the structural filler particles by separating particles from clusters, decreases the size of the structural filler particles, eliminates large particles by breakage and increases the specific surface area of the structural filler particles by producing a large quantity of very fine particles. Size reduction with an agitator mill or vibratory mill occurs due to a combination of impact with the milling media, abrasion with the milling media and attrition of the particles.

Structural fillers suitable for use in the present invention include barium magnesium aluminosilicate glass, barium aluminoborosilicate glass (BAG), amorphous silica, silica-zirconia, silica-titania, barium oxide, quartz, alumina and other inorganic oxide particles. The mean particle size of the structural filler is limited to less than the wavelength of light to prevent the structural filler from decreasing surface gloss after substantial brushing. However, it is expected that as the particle size is reduced below about 0.05 $\mu$m the strength needed for load-bearing restorations demises due to increasing occluded volume of resin. Currently, it is believed that a mean particle size between about 0.05 $\mu$m and about 0.5 $\mu$m provides the best balance between optical and structural properties.

Nanofillers suitable for use in the present invention include powders with particles that are not aggregated or substantially agglomerated so as to minimize particle-particle interactions. The discrete particles have a mean particle size less than 100 nm. By "discrete particles," there are included weakly agglomerated particles having an agglomerated average size less than 100 nm. For example, Nanomaterials Research Corp., Longmont, Colo., manufactures an aluminosilicate powder having a mean particle size of about 80 nm and a 1:4 molar ratio of alumina to silica. This nanofiller has a refractive index of 1.508.

By way of further example, Nalco Chemical Co., Naperville, Ill., provides nanofiller particles having a mean particle size of about 20 nm, which are sold under the commercial designation of Nalco 2327. This nanofiller has a refractive index of 1.48. By way of yet a further example, Nanophase Technologies Corp., Romeoville, Ill., manufactures gamma alumina powders having mean particle sizes less than 20 nm, as well as a powder having a mean particle size of 38 nm. This nanofiller has a refractive index of about 1.71. The powder is produced by a physical vapor synthesis process, such as that described in U.S. Pat. Nos. 5,874,684; 5,514,349; and 5,460,701, each incorporated by reference herein in its entirety.

The nanofiller particles may be surface treated, for example with gamma methacryloxypropyltrimethoxy silane (MEMO). The nanofiller comprises at least about 0.01% by volume of the dental composite, more advantageously about 1–15% by volume, and most advantageously about 5–12% by volume.

Generally, the nanofiller should have a refractive index similar to that of the resin. Resins typically have a refractive index of about 1.48–1.55. Thus, the nanofiller should have a refractive index in the range of about 1.48–1.6. However, it is believed that for nanofillers of 20 nm particle size or less, the refractive index may vary from that of the filler without negatively affecting the optical properties of the dental composite.

Prepolymerized fillers suitable for use in the present invention include particles having an inorganic portion and a polymerized organic resin portion. Advantageously, the inorganic portion is greater than the organic portion. The prepolymerized filler is present in the composite in an amount of at least about 1% by volume, and advantageously between about 1% and about 60% by volume, and more advantageously between about 10% and 40% by volume. A proper balance between the prepolymerized filler and ground structural filler enhances the polydispersity of the composite paste, which provides higher loading capability and improves the handling properties of the paste. In addition, higher loading reduces the hydrodynamic drag and viscosity of the uncured composite.

Figure 1:
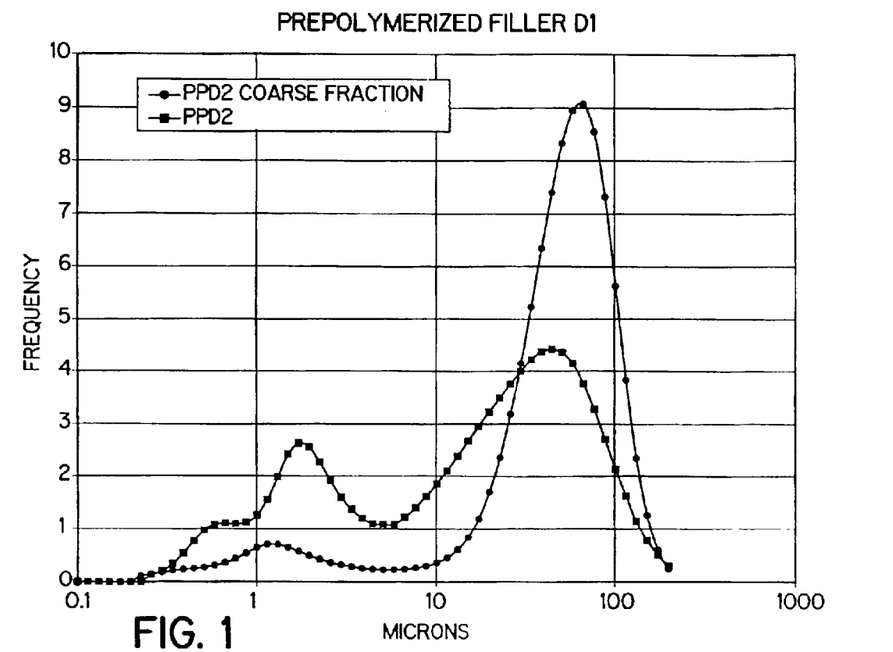
FIGS. 1 and 2 are particle size distributions for two exemplary prepolymerized fillers used in composites of the present invention, each including an unclassified bimodal filler and a classified coarse filler.
Figure 2:
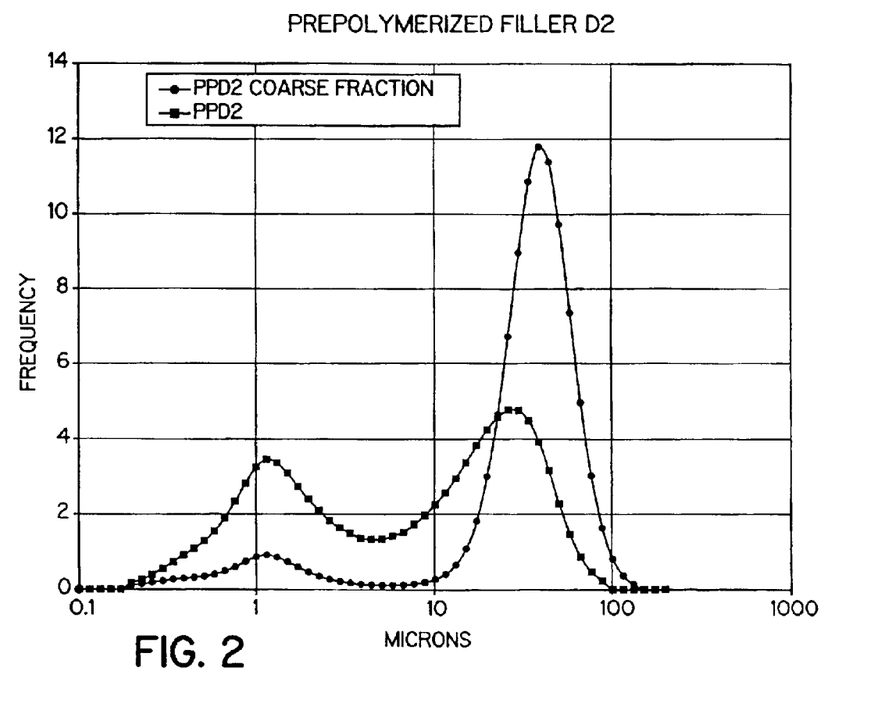

The prepolymerized filler for use in the present invention may be prepared by a variety of conventional methods and may comprise filler materials traditionally used as reinforcing filler and/or microfiller and resins typically used for restorative composites. For example, fumed silica and BAG or other filler of desired size and characteristics may be mixed with polymerizable resin to prepare a paste. The paste is then heat polymerized and the resultant polymerized mass is ground to the desired particle size, for example, using a ceramic ball mill. Where the inorganic portion comprises a mixture of reinforcing filler and microfiller, the particles size distribution of the prepolymerized filler will likely be generally bimodal. For example, for a mixture of 40 nm microfiller and 0.7 $\mu$m reinforcing filler, a small (fine) particles size fraction will have a distribution centered around about 1–3 $\mu$m, and a large (coarse) particle size fraction will have a distribution centered around about 30–70 $\mu$m in size, with a volume ratio of approximately 30:70 percent, respectively. In an exemplary embodiment, at least about 90% of the particles of the prepolymerized filler have a size below about 100 $\mu$m, and advantageously at least about 95% are below about 100 $\mu$m. Particle size distributions for two exemplary prepolymerized fillers having a bimodal size distribution are shown in FIGS. 1 and 2, and are referred to as PPD1 and PPD2.

A further reduction in shrinkage may be obtained by separating the small (fine) and large (coarse) particle size fractions and using the coarse particle fraction for the prepolymerized filler. An air classifier may be used to separate the fractions, such as a Cyclo-Tex, KC-21 model available commercially from Cyclotex Inc., Rancho Dominguez, Calif., which is of cast iron construction and has a variable speed drive. The Cyclo-Tex machine is designed to operate with abrasive materials, and is grounded. The internal components are made mostly of stainless steel, low carbon steel, and urethane. Tungsten carbide wear blocks and tungsten carbide plasma spray is on many of the wear surfaces. The coarse discharge tubes are composed of TYGON® and the fine discharge connector tube is made of urethane. Using the classifier, the coarse or large fraction is collected, and comprises particles mostly above 10 $\mu$m, and an average particle size of about 30–70 $\mu$m. The coarse fraction advantageously contains less than about 15% by volume of particles smaller than 10 $\mu$m. Referring to FIGS. 1 and 2, the coarse fraction of the air classified PPD1 and PPD2 are shown. It may be appreciated, however, that the particle size distribution will vary depending upon the starting materials used for the inorganic portion and the method of grinding.

The inclusion of a prepolymerized filler into a composite having a ground structural filler and a discrete, non aggregated nanofiller will minimize or reduce the total shrinkage of the composite when it is cured. Composites prepared and tested, as set forth in the examples below, reveal drastic reduction in composite shrinkage when compared to composites of the prior art. Shrinkages have ranged from about 2% and less upon curing of the composites of the present invention. Both axial and volumetric shrinkages may be less than 2%, and even as low as about 1.5–1.6% in the case of axial shrinkage measured at 60 seconds. Less shrinkage has tremendous benefits including prolonging the stability and strength of the cured composite while decreasing the need for repairs and replacement. Specifically, lower shrinkage during curing results in a smaller percentage of separation between the restoration and tooth structure. The result is a composite material with high tooth-composite marginal integrity, which in turn maximizes restorative longevity and minimizes secondary caries. Furthermore, inclusion of a prepolymerized filler decreases the viscosity of the uncured composite thereby improving its handling properties and adding convenience to the dental practitioner.

The present invention will be further appreciated in light of the following examples.

EXAMPLES

Five composite examples, including two comparative samples and three test samples, were prepared to illustrate the benefits of including prepolymerized filler in composites comprising a structural filler and a nanofiller. Test Samples 1–3 include ground structural filler, a 20 nm discrete nanofiller and prepolymerized filler in accordance with the present invention. Comparative Sample 1 includes ground structural filler and 20 nm and 40 nm nanofillers (microfillers) of the prior art. Comparative Sample 2 includes ground structural filler, a 20 nm discrete nanofiller and a 20 nm nanofiller (microfiller) of the prior art. The five composites were prepared as described below.

To prepare the structural filler for inclusion into the five dental composites, the filler material to be milled, in this case BAG (barium alumino-borosilicate glass, type SP-345, Specialty Glass, Oldsmar, Fla.), was charged into a vibratory mill from Sweco (Florence, Ky.), as described in U.S. Pat. Nos. 5,979,805 and 6,098,906, incorporated herein by reference in their entirety. The vibratory mill was filled with glass media and water, and the mill was vibrated to comminute the particles.

When the filler slurry is removed from the mill, the mean particle size is measured, typically by laser scattering. Laser scattering is a method of measuring mean particle size by sensing the average relative angular intensity of scattered light. A beam of monochromatic light with a uniform wave front is directed at the sample, the light is diffracted or scattered by the particles and a detector is used to measure the relative average intensity of the scattered light at various angles. The mean particle size and size distribution may then be calculated from the relative average intensity. One such laser scattering device is disclosed in U.S. Pat. No. 5,610,712 to Schmitz et al., incorporated herein by reference in its entirety. For the present example, a Horiba Model 2A-910 Laser Scattering Mean Particle Size Analyzer was used. The resulting structural filler is as follows: 10% by volume of the filler particles have a mean particle size of less than 0.28 μm; 50% by volume of the filler particles have a mean particle size less than 0.44 μm; and 90% by volume of the filler particles have a mean particle size less than 0.66 μm. This filler is referred to henceforth as a 0.4 μm structural filler.

The slurry was then dried at 110° C. and the dried cake was sieved through a 100 mesh (150 μm) plastic screen. The ground glass was then silanated by spraying in a V-blender with a 20% hydrolyzed solution of MEMO in water to make the powder hydrophobic. The loading of the silane in the filler was 2.5% by weight.

The prepolymerized filler for inclusion in Test Samples 1 and 2 was prepared with the components listed in Table 2. First, Resin 2 listed in Table 1 was combined with a 0.7 μm silane treated BAG filler and a 40 nm silane treated fumed silica and mixed in a planetary mixer followed by deaeration to form a paste. The paste was then layered into sheets and heat polymerized for 4 hours in a convection oven heated to 100° C. The resultant polymerized mass was ground using a ceramic ball mill to give prepolymerized filler particles having a particle size distribution as shown in FIG. 1., referred to as PPD1. The fine particle fraction has an average particle size of about 1.8, and the course particle fraction has an average particle size of about 40 μm.

The prepolymerized filler for inclusion in Test Sample 3 was prepared using the coarse fraction of the PPD1 filler used in Test Samples 1 and 2, the coarse fraction obtained using the air classifier Cyclo-Tex, KC-21 described above. The PPD1 filler was run in an open atmosphere, and hand fed at a low feed rate. The classifier was operated at 4500 rpm, with a 5% throttle opening and a 2 hole (1⅜ inch each) air inlet restrictor plate. A large blower (5 horsepower, 3500 rpm, radial blade) was running through a bag house filter. The coarse fraction size distribution is shown in FIG. 1.

The discrete nanofiller used for the Test Samples 1–3 and Comparative Sample 2 was Nalco 2327 made of silica and having a diameter of about 20 nm. The nanofiller particles are discrete and non-aggregated. The nanopowder was first treated as follows: In a 10 inch drying dish, 250 g Nalco 2327 slurry, 300 g methoxypropanol (Dowanol® PM from Dow Chemical Co.) and 3.8 g MEMO were stirred for 30 min., followed by evaporation at 80° C. at 80 mbar for 5 hours and then for 16 hours at 80° C. and 1–2 mbar. The resultant residue was screened through a 90 μm plastic screen. The prior art nanofillers (microfillers) included in Comparative Samples 1 and 2 were hydrophobic fumed silicas, specifically US202 (available commercially from Degussa Corp., Ridgefield Park, N.J.), having an average particle size of 20 nm (Comparative Samples 1 and 2) and OX-50 (also available commercially from Degussa Corp., Ridgefield Park, N.J.) having an average particle size of 40 nm (Comparative Sample 1). The OX-50 was silanated by spraying in a V-blender with a 20% hydrolyzed solution of MEMO in water to make the powder hydrophobic. The loading of the silane in the OX-50 was 5% by weight.

The 0.4 μm structural filler, the prepolymerized filler, and/or the nanofillers are then combined with a light-curable resin base material which may include commercially available monomers containing methacrylate groups. TABLE 1 lists the components of the resins that were used in the five composites. Pigments such as titanium dioxide may be added to control optical properties of the composite.

TABLE 1

RESIN COMPOSITIONS

| COMPONENT | Resin 1 (Wt. %) | Resin 2 (Wt. %) | Resin 3 (Wt. %) |
| --- | --- | --- | --- |
| BisGMA (Bisphenol A Diglycidyl ether dimethacrylate) | 3.0 | 49.4 | 10.0 |
| Ethoxylated Bisphenol A dimethacrylate (No. of ethoxy groups = 3.5) | 71.1 | — | 24.6 |
| Ethoxylated Bisphenol A dimethacrylate (No. of ethoxy groups = 6.0) | — | — | 59.2 |
| Triethylene Glycol Dimethacrylate | 24.7 | 49.4 | 5.0 |
| Benzoyl peroxide | — | 0.75 | — |
| 2-Ethylhexyl-4-(dimethylamino)benzoate | 0.49 | — | 0.49 |
| Camphorquinone | 0.17 | — | 0.17 |
| 2-Hydroxy-4-methoxy Benzophenone | 0.49 | 0.49 | 0.49 |
| Butylated Hydroxytoluene (BHT) | 0.05 | 0.05 | 0.05 |
| TOTAL | 100 | 100 | 100 |
| Viscosity, at 25° C. (Pa · s) | 0.15 | — | 0.59 |
| Refractive Index | 1.518 | 1.508 | 1.529 |

TABLE 2

PREPOLYMERIZED FILLER COMPOSITIONS

| | |
|---|---|
| Wt. % 0.7 µm BAG Filler | 70 |
| Wt. % OX-50 Fumed Silica | 5 |
| Wt. % Resin 2 (Table 1) | 25 |
| TOTAL | 100 |
| Volume % Inorganic Load | 54.6 |

Other monomers may be used in the resin composition, such as diethylene glycol dimethacrylate, tetraethylene glycol dimethacrylate, 1,12-dodecanediol dimethacrylate, diurethane dimethacrylate (Rohamere 6661-0, Huls America, Somerset, N.J.), trimethylolpropane trimethacrylate, glyceryl dimethacrylate, and neopentylglycol dimethacrylate.

The resin is introduced into a planetary mixer thermostated at 50° C. A polycaprolactone-modified methacrylate monophosphate dispersant was added to the resin in an amount of 2 wt. % in accordance with U.S. Pat. No. 6,300,390, incorporated by reference herein in its entirety. Specifically, a polycaprolactone-modified ethyl methacrylate phosphate dispersant was used, which was prepared with a 5:1 molar ratio of caprolactone units to hydroxyethyl methacrylate, followed by phosphorylation. The planetary mixer is then started and the filler containing the physically admixed components listed in Table 3 below are added slowly over a period of three hours. The composite is subsequently mixed for another hour and then de-aerated under attenuated oxygen pressure.

In forming a restoration using the composite of the present invention, the surface of the tooth is prepared by removing any portion of the tooth enamel, and if necessary the dentin, that is decayed or damaged. A retention groove is then formed in the dentin if needed to maintain the restoration on the tooth. The practitioner then adds opacifiers and pigments to match the color of the composite with the color of the tooth. The composite is then built up on the surface of the tooth to replace any lost material. Once the practitioner is satisfied with the appearance of the restoration the composite is exposed to a visible light source to cure the resin and activate the adhesive by cross-linking the polymer matrix. After the composite has been cured, the surface is polished.

Testing

TABLE 3 provides the testing results of the four composites. All measurements were carried out using standard ISO methods except where indicated, and the standard deviations are provided in parentheses. Standard ISO method 4049 for resin-based filling materials was used whenever possible.

TABLE 3

| | Comparative Sample 1 | Comparative Sample 2 | Test Sample 1 | Test Sample 2 | Test Sample 3 |
|---|---|---|---|---|---|
| Resin | Resin 1 | Resin 1 | Resin 3 | Resin 3 | Resin 3 |
| Wt. % Nanofiller (Vol. %) | 4% OX-50 + 3% US202 (6.5) | 12% Nalco 2327[1] + 2% US202 (13.3) | 11.7% Nalco 2327[1] (10.6) | 12% Nalco 2327[1] (10.9) | 12% Nalco 2327[1] (11) |
| Wt. % Prepolymerized Filler (Vol. %) | 0 | 0 | 26.38 (26.5) | 26.5 (26.4) | 27 (27.1) |
| Wt. % 0.4 µm BAG[2] filler (Vol. %) | 69.5 (50.2) | 66 (49.0) | 44.9 (32) | 44.5 (31.7) | 44.5 (31.8) |
| Wt. % Dispersant | 2 | 2 | 2 | 2 | 2 |
| Wt. % Total Load (Vol. %) | 76.5 (56.7) | 80.0 (62.3) | 83.0 (69.0) | 83.0 (69.0) | 83.5 (69.9) |
| Wt. % Total Inorganic Load (Vol. %) | 76.5 (56.7) | 80.0 (62.3) | 76.4 (57.1) | 76.4 (57.1) | 76.41 (57.1) |
| % Translucency[3] | 35.0 | 41.0 | 40.1 | 39 | — |
| Vicker's Hardness[4] (N/mm$^2$) | 585 (7) | 702 (10) | 518 (2) | 595 (3) | 598 (3) |
| Flexural Strength (MPa) | 126 (18) | 121 (11) | 93 (8) | 118 (9) | 134 (11) |
| Flexural Modulus (MPa) | 10004 (362) | 11667 (219) | 9854 (406) | 11009 (489) | 12057 (570) |
| % Axial shrinkage at 60 sec[5] | 2.71 (0.08) | 2.26 (0.04) | 1.52 (0.03) | 1.57 (0.04) | 1.45 (0.04) |
| % Axial shrinkage at 10 sec[5] | 2.29 (0.07) | 1.87 (0.04) | 1.23 (0.04) | 1.18 (0.01) | 1.10 (0.07) |
| % Axial shrinkage at 5 sec[5] | 1.65 (0.05) | 1.45 (0.04) | 0.93 (0.05) | 0.89 (0.01) | 0.86 (0.07) |
| % Volumetric shrinkage (Buoyancy Method[6]) | 3.11 (0.01) | — | — | 1.82 (0.07) | 1.58 (0.06) |
| Gloss, 60 degrees[7] | 32.5 (1.9) | — | — | 41 (0.5) | 40.5 (0.6) |
| Penetrometer (mm) 0 g, 1 mm flathead[8] | >8.0 | 5.4 | 2.9 | 2.5 | 1.3 |

[1]5% MEMO coated.
[2]BAG-Barium Aluminosilicate Glass.
[3]Samples 20 mm in diameter and 1 mm in thickness were cured on each side for 60 seconds with a tungsten halogen lamp. The translucency was then measured in the transmission mode using a TCS Colorimeter (BYK-Gardner, Columbia, MD), by recording the Y value after the sample was placed on the transmission accessory.
[4]Average of 3 measurements on the top surface of a cylindrical sample 10 mm in diameter and 2 mm in height. The samples were light cured for 40 seconds and stored in water for 24 hours at 37° C. prior to measurement.
[5]The bonded disk method of D.C. Watts and A.J. Cash (Dent. Mater. 7,281 (1991)) was used. A 157 mm$^3$ disk-shaped sample of paste is sandwiched between a cover glass plate 1.8 mm thick and a glass cover slip of 0.2 mm thick. A non-contact brass ring-shaped spacer 1.0 mm thick is used. On top, an LDVT transducer with a 2 g probe mass is in contact with the glass slip and measures the dimensional change after polymerization for 20 seconds from a Demetron 401 dental curing light with an 11 mm tip situated underneath the glass plate. The measurement after 5, 10 and 60 seconds is recorded.
[6]Buoyancy method in water was used. The shrinkage was measured by the difference of densities before and after cure for a 0.5 g disk-shaped sample. The average of 3 samples is reported.
[7]Cured samples were prepared with the dimensions of 20 × 40 × 2 mm and were sanded with wet #600 silicon carbide paper (3M, St. Paul, MN) under water until a constant gloss value was obtained. A Leco Spectrum 2000 grinder and polisher (St. Joseph, MI) was used with an orbital speed of 80 rpm and a head speed of 25 rpm for 1.5 min. and 3 lbs of pressure. The gloss of the surface was measured using a Micro-Tri-Gloss apparatus (BYK-Gardner USA, Columbia, MD), which performs a photoelectric measurement of specularly reflected light from a surface. This instrument was calibrated according to ISO standard 2813. The measurement angle was 60 degrees. An average of three measurements is reported.
[8]Precision Penetrometer (GCA Corp., Chicago, IL) with a 1 mm flat head was used with no additional weight (0 g). The paste was placed in a mold 10 mm in diameter and 8 mm in height. Penetration was performed for 10 seconds. An average of 3 measurements is reported.

For the comparative sample 2 containing the 0.4 µm structural filler and a discrete nanofiller, an increase in filler loading and reduction in shrinkage is achieved compared to the comparative sample 1 with the same structural filler but a nanofiller of the prior art. For the test dental composites containing a 0.4 µm structural filler, a prepolymerized filler, and a discrete nanoparticle filler, in accordance with the present invention, the addition of prepolymerized filler led to an even greater increase in filler loading capacity and a significant reduction in shrinkage. Particularly, both the axial and volumetric shrinkage was reduced by about 25% or more from the comparative composites. The reduction in shrinkage observed in the above examples is believed to be attributable at least in part to the higher volume loading. Advantageously, composites of the present invention have a volume loading greater than about 65%. In addition, composites including the prepolymerized fillers in accordance with the present invention resulted in lower viscosity, as evidenced by the penetrometer measurements.

The total filler loading for composites of the present invention includes a portion that is inorganic and a portion that is organic. The organic portion is the resin in the prepolymerized filler, and the inorganic portion is the remainder, e.g., the BAG and silica. The comparative samples do not have an organic portion contributing to the filler loading. The total inorganic load of the test samples was approximately the same as the inorganic load and the total load of Comparative Sample 1, yet the test samples exhibited drastically lower shrinkage. The reduction in shrinkage can thus be at least partially attributed to the prepolymerized filler, and more specifically, to the presence of an organic portion in the filler. It is also notable that higher gloss was obtained in the Test Samples compared to Comparative Sample 1, despite the use of 0.7 µm BAG filler in the prepolymerized filler component.

In addition, Test Sample 3, which used the air classified coarse fraction of the bimodal prepolymerized filler exhibited even lower shrinkage than Test Samples 1 and 2, which used the unclassified fine and coarse fractions of the bimodal prepolymerized filler. An increase in hardness, flexural strength and flexural modulus was also observed, as well as lower viscosity as evidenced by the penetrometer measurement.

The tests described above used small-scale prepared pastes and the formulas were not especially optimized with respect to the extent of mixing. More intense mixing methods and variations in the nanoparticle surface treatment are expected to further increase volume loading of the fillers, which is likewise expected to lead to further reduction in shrinkage. Also, it should be understood that the translucency of a paste increases typically upon aging due to "wetting out" of the filler. This "wetting out" effect is expected to be more pronounced with nanofillers due to the smaller inclusions between them for which the resin takes longer to enter.

Thus, the dental composite of the present invention provides a restoration having the high strength from high filler loading and reduced shrinkage upon curing while providing translucency and surface gloss useful in cosmetic restorations. Through the use of structural filler particles having a mean particle size less than the wavelength of light, yet large enough to provide strength, the dental composite of the present invention provides the luster and translucency of dispersion reinforced composites with the strength of hybrid composites. Through the use of prepolymerized filler in combination with discrete, non-aggregated nanoparticles and the structural filler, improved physical properties may be obtained, and significantly less shrinkage occurs upon polymerization.

While the present invention has been illustrated by a description of various embodiments and while these embodiments have been described in considerable detail, it is not the intention of the Applicants to restrict or in any way limit the scope of the appended claims to such detail. Additional advantages and modifications will readily appear to those skilled in the art. The invention in its broader aspects is therefore not limited to the specific details and representative compositions as shown and described. This has been a description of the present invention, along with the preferred composition using the present invention as currently known. However, the invention itself should only be defined by the appended claims.

What is claimed is:

1. A dental composite, comprising:
   a polymerizable resin base; and
   about 10% by volume to about 80% by volume filler consisting essentially of a structural filler, a prepolymerized filler, and a nanofiller,
   wherein the structural filler comprises between about 10% by volume and about 70% by volume of the composite and consists of ground particles of mean particle size between about 0.05 µm and about 0.50 µm, and wherein the ground structural filler contains less than 50% by volume of particles above 0.5 µm in diameter,
   wherein the prepolymerized filler comprises at least about 1% by volume of the composite and consists of an inorganic portion and a polymerized organic resin portion, and
   wherein the nanofiller comprises at least about 0.01% by volume of the composite and consists essentially of discrete, non-aggregated particles of mean particle size less than about 100 nm.

2. The dental composite of claim 1, wherein the axial shrinkage of the composite after 60 seconds of polymerization is about 2% or less, as measured by the bonded disk method.

3. The dental composite of claim 1, wherein the volumetric shrinkage of the composite during polymerization thereof is about 2% or less, as measured by the water buoyancy method.

4. The dental composite of claim 1, wherein the resin base comprises a polymerizable vinyl compound.

5. The dental composite of claim 1, wherein the prepolymerized filler comprises between about 10% and about 40% by volume of the composite.

6. The dental composite of claim 1, wherein the nanofiller comprises between about 5% and about 12% by volume of the composite.

7. The dental composite of claim 1, wherein the nanofiller consists essentially of discrete particles selected from the group consisting of aluminosilicate particles, gamma alumina particles, silica particles, and combinations thereof.

8. The dental composite of claim 7, wherein the nanofiller consists essentially of silica particles having a mean particle size of about 20 nm or less.

9. The dental composite of claim 7, wherein the nanofiller consists essentially of aluminosilicate particles having a mean particle size of about 80 nm or less.

10. The dental composite of claim 7, wherein the nanofiller consists essentially of gamma alumina particles having a mean particle size of about 20 nm or less.

11. The dental composite of claim 1, wherein the prepolymerized filler consists essentially of particles having a particle size distribution including a mean particle size in the range of about 30 µm to about 70 µm, at least about 90% of the particles of size less than about 100 μm, and at least about 85% of the particles of a size greater than about 10 μm.

12. The dental composite of claim 1, wherein the prepolymerized filler consists essentially of particles having a bimodal particle size distribution including a fine particle fraction of mean particle size in the range of about 1 μm to about 3 μm and a coarse particle fraction of mean particle size in the range of about 30 μm to about 70 μm, at least about 95% of the particles of size less than about 100 μm.

13. The dental composite of claim 1, wherein the prepolymerized filler particles comprise silica as the inorganic portion and a methacrylate base resin as the polymerized organic resin portion.

14. A dental composite comprising:
a polymerizable resin base; and
about 22% by volume to about 80% by volume filler in the resin base, the filler consisting essentially of a ground structural filler, a prepolymerized filler, and a nanofiller;
wherein the ground structural filler comprises between about 20% by volume and about 70% by volume of the composite and consists of ground particles having a mean particle size of between about 0.05 μm and about 0.50 μm,
wherein the prepolymerized filler comprises from about 1% to about 60% by volume of the composite and consists essentially of ground polymerized particles having an inorganic portion and a polymerized organic resin portion and a particle size distribution having at least a first average particle size peak centered in the range of about 30 μm to about 70 μm,
wherein the nanofiller comprises between about 1% by volume and about 15% by volume of the composite and consists essentially of discrete, non-aggregated particles having a mean particle size of less than about 100 nm; and
wherein volumetric shrinkage of the composite during polymerization thereof is about 2% or less, as measured by the water buoyancy method.

15. The dental composite of claim 13, wherein the axial shrinkage of the composite after 60 seconds of polymerization is about 2% or less, as measured by the bonded disk method.

16. The dental composite of claim 14, wherein the prepolymerized filler consists essentially of particles having at least about 90% of the particles of size less than about 100 μm, and at least about 85% of the particles of a size greater than about 10 μm.

17. The dental composite of claim 14, wherein the prepolymerized filler consists essentially of particles having a bimodal particle size distribution including a second average particle size peak centered in the range of about 1 μm to about 3 μm and at least about 95% of the particles of size less than about 100 μm.

18. The dental composite of claim 14, wherein the resin base includes a polymerizable vinyl compound.

19. A dental composite, comprising:
a polymerizable resin base; and
about 35% by volume to about 80% by volume filler consisting essentially of a ground structural filler, a prepolymerized filler, and a nanofiller;
wherein the ground structural filler comprises between about 20% by volume and about 60% by volume of the composite and consists of ground particles of mean particle size between about 0.05 μm and about 0.50 μm, and wherein the ground structural filler contains less than 50% by volume of particles above 0.5 μm in diameter,
wherein the prepolymerized filler comprises between about 10% and about 40% by volume of the composite and consists essentially of ground polymerized particles having an inorganic portion and a polymerized organic resin portion and having a mean particle size in the range of from about 30 μm to about 70 μm, and wherein the prepolymerized filler contains at least about 90% of the particles of size less than about 100 μm, and at least about 85% of the particles of a size greater than about 10 μm, and
wherein the nanofiller comprises between about 5% by volume to about 12% by volume of the composite and consists essentially of discrete, non-aggregated particles of mean particle size less than about 50 nm.

20. The dental composite of claim 19, wherein the nanofiller consists essentially of silica particles having a mean particle size of about 20 nm.

21. The dental composite of claim 19, wherein the axial shrinkage of the composite after 60 seconds of polymerization is about 2% or less, as measured by the bonded disk method.

22. A method of making a dental composite paste for use in restoring a tooth, the method comprising:
preparing a prepolymerized filler by mixing an inorganic filler with an organic polymerizable resin, curing the mixture, and then grinding the cured mixture;
providing a structural filler consisting of ground particles of mean particle size between about 0.05 μm and about 0.50 μm, and wherein the ground structural filler contains less than 50% by volume of particles above 0.5 μm in diameter;
providing a discrete nanofiller consisting essentially of discrete, non-aggregated particles of mean particle size less than about 100 nm;
mixing the structural filler, prepolymerized filler and discrete nanofiller with a polymerizable resin base to form a dental composite paste having a total filler loading between about 10% by volume and about 80% by volume, wherein the structural filler comprises between about 10% by volume and about 70% by volume of the composite paste, the prepolymerized filler comprises at least about 1% by volume of the composite paste, and the discrete nanofiller comprises at least about 0.01% by volume of the composite paste; and
wherein, upon curing, the dental composite paste is adapted to exhibit about 2% or less volumetric shrinkage, as measured by the water buoyancy method.

23. The method of claim 22, wherein the prepolymerized filler comprises between about 1% and about 60% by volume of the composite paste.

24. The method of claim 22, wherein the nanofiller comprises between about 1% and about 15% by volume of the composite paste.

25. The method of claim 22, wherein the nanofiller provided consists essentially of discrete particles selected from the group consisting of aluminosilicate particles, gamma alumina particles, silica particles, and combinations thereof.

26. The method of claim 25, wherein the nanofiller provided consists essentially of silica particles having a mean particle size of about 20 nm or less.

27. The method of claim 25, wherein the nanofiller provided consists essentially of aluminosilicate particles having a mean particle size of about 80 nm or less.

28. The method of claim 25, wherein the nanofiller provided consists essentially of gamma alumina particles having a mean particle size of about 20 nm or less.

29. The method of claim 22, wherein the prepolymerized filler after grinding consists essentially of particles having a bimodal particle size distribution including a fine particle fraction and a course particle fraction, the method further comprising classifying the particles to separate the coarse particle fraction from the fine particle fraction to provide the prepolymerized filler with a coarse particle size distribution including a mean particle size in the range of about 30 μm to about 70 μm, at least about 90% of the particles of size less than about 100 μm, and at least about 85% of the particles of a size greater than about 10 μm.

30. The method of claim 22, wherein the prepolymerized filler after grinding consists essentially of particles having a bimodal particle size distribution including a fine particle fraction of mean particle size in the range of about 1 μm to about 3 μm and a coarse particle fraction of mean particle size in the range of about 30 μm to about 70 μm, at least about 95% of the particles of size less than about 100 μm.

31. The method of claim 22, wherein the inorganic filler comprises silica and the organic polymerizable resin comprises a polymerizable methacrylate base resin.

32. The method of claim 22, wherein, upon curing, the dental composite paste is adapted to exhibit about 2% or less axial shrinkage, as measured by the bonded disk method.

33. The method of claim 22, wherein the prepolymerized filler comprises between about 10% and about 40% by volume of the composite paste and consists essentially of ground polymerized particles having a mean particle size of between about 30 μm and 70 μm.

34. The method of claim 22, wherein the resin base comprises a polymerizable vinyl compound.

35. The method of claim 22, wherein the nanofiller comprises between about 5% and about 12% by volume of the composite paste.

36. A method of restoring a tooth, the method comprising:
mixing a structural filler, a prepolymerized filler and a discrete nanofiller with a polymerizable resin base to form a dental composite paste having between about 10% by volume and about 80% by volume total filler loading,
wherein the structural filler comprises between about 10% by volume and about 70% by volume of the composite paste, and consists of ground particles of mean particle size between about 0.05 μm and about 0.50 μm, and wherein the ground structural filler contains less than 50% by volume of particles above 0.5 μm in diameter, and
wherein the prepolymerized filler comprises at least about 1% by volume of the composite paste, and consists essentially of an inorganic portion and a polymerized organic resin portion, and
wherein the nanofiller comprises at least about 0.01% by volume of the composite paste, and consists essentially of discrete, non-aggregated particles of mean particle size less than about 100 μm;
applying the dental composite paste to the tooth to be restored; and
curing the dental composite paste, wherein the volumetric shrinkage of the cured dental composite is about 2% or less, as measured by the water buoyancy method.

37. The method of claim 36, wherein the prepolymerized filler comprises between about 1% and about 60% by total volume of the composite paste.

38. The method of claim 36, wherein the nanofiller comprises between about 1% and about 15% by total volume of the composite paste.

39. The method of claim 36, wherein the nanofiller consists essentially of discrete particles selected from the group consisting of aluminosilicate particles, gamma alumina particles, silica particles, and combinations thereof.

40. The method of claim 39, wherein the nanofiller consists essentially of silica particles having a mean particle size of about 20 nm or less.

41. The method of claim 39, wherein the nanofiller consists essentially of aluminosilicate particles having a mean particle size of about 80 nm or less.

42. The method of claim 39, wherein the nanofiller consists essentially of gamma alumina particles having a mean particle size of about 20 nm or less.

43. The method of claim 36, further comprising preparing the prepolymerized filler, prior to forming the dental composite paste, by mixing an inorganic filler and a polymerizable organic resin, curing the mixture, and then grinding the cured mixture to consist essentially of particles having a bimodal particle size distribution including a fine particle fraction of mean particle size in the range of about 1 μm to about 3 μm and a coarse particle fraction of mean particle size in the range of about 30 μm to about 70 μm, at least about 95% of the particles of size less than about 100 μm.

44. The method of claim 43, further comprising air classifying the particles to separate the fine particle fraction from the coarse particle fraction to provide the prepolymerized filler with a coarse particle size distribution including a mean particle size in the range of about 30 μm to about 70 μm, at least about 90% of the particles of size less than about 100 μm, and at least about 85% of the particles of a size greater than about 10 μm.

45. The method of claim 44, wherein the inorganic filler comprises silica and boroaluminosilicate glass and the polymerizable organic resin portion comprises a methacrylate base resin.

46. The method of claim 36, wherein the axial shrinkage of the cured dental composite paste is about 2% or less, as measured by the bonded disk method.

47. The method of claim 36, wherein the prepolymerized filler comprises between about 10% and about 40% by volume of the composite paste and consists essentially of ground polymerized particles having a mean particle size of between about 30 μm and 70 μm.

48. The method of claim 36, wherein the resin base comprises a polymerizable vinyl compound.

49. The method of claim 36, wherein the nanofiller comprises between about 5% and about 12% by volume of the composite paste.

* * * * *

UNITED STATES PATENT AND TRADEMARK OFFICE
CERTIFICATE OF CORRECTION

PATENT NO.        : 6,890,968 B2
APPLICATION NO. : 10/234594
DATED             : May 10, 2005
INVENTOR(S)      : Christos Angeletakis et al.

It is certified that error appears in the above-identified patent and that said Letters Patent is hereby corrected as shown below:

Column 15, lines 54-55 read "…of discrete, non-aggregated particles of mean particle size less than about 100 µm;…" and should read -- …of discrete, non-aggregated particles of mean particle size less than about 100 nm;… --.

Drawings, Fig 1, Key reads "PPD2 COARSE FRACTION and PPD2" and should read -- … PPD1 COARSE FRACTION and PPD1… --.

Signed and Sealed this

Fifth Day of September, 2006

JON W. DUDAS
*Director of the United States Patent and Trademark Office*